United States Patent [19]

Hall

[11] Patent Number: 4,848,347
[45] Date of Patent: Jul. 18, 1989

[54] INTERFERENTIAL ELECTRICAL CURRENT THERAPY SYSTEMS AND METHODS

[75] Inventor: Duane O. Hall, Sandy, Utah

[73] Assignee: Dynatronics Laser Corporation, Salt Lake City, Utah

[21] Appl. No.: 177,569

[22] Filed: Apr. 4, 1988

[51] Int. Cl.⁴ .............................................. A61N 1/36
[52] U.S. Cl. .................................. 128/420 A; 128/422
[58] Field of Search ................ 128/420 A, 422, 420 R

[56] References Cited

U.S. PATENT DOCUMENTS

| | | | |
|---|---|---|---|
| 3,096,768 | 7/1963 | Griffith, Jr. | 128/420 A |
| 3,774,620 | 11/1973 | Hansjurgens | 128/420 |
| 3,895,639 | 7/1975 | Rodler | 128/422 |
| 3,958,577 | 5/1976 | Rodler | 128/420 A |
| 4,023,574 | 5/1977 | Nemec | 128/420 A |
| 4,071,033 | 1/1978 | Nawracaj et al. | 128/420 A |
| 4,153,061 | 5/1979 | Nemec | 128/420 A |
| 4,280,504 | 7/1981 | Rodler | 128/420 A |

*Primary Examiner*—Lee S. Cohen
*Attorney, Agent, or Firm*—Berne S. Broadbent

[57] ABSTRACT

A system and method for interferential electrical current therapy wherein the region of beneficial interference may be positioned in the body of a patient by selectively controlling the electrical signal which is provided to each of two pairs of electrodes secured to the patient's body. Two electrical signals are provided which have frequencies that differ by a predetermined amount. The system comprises means for selectively amplifying, phase shifting, and mixing the second electrical signal with the first electrical signal and applying the mixed signal to a first pair of electrodes. The system further comprises means for selectively amplifying, phase shifting, and mixing the first electrical signal with the second electrical signal and applying the mixed signal to a second pair of electrodes.

15 Claims, 4 Drawing Sheets

INTERFERENTIAL ELECTRICAL CURRENT THERAPY SYSTEMS AND METHODS

BACKGROUND

1. The Field of the Invention

This invention relates to interferential electrical current therapy devices and, more particularly, to novel systems and methods for positioning the region of beneficial interference in a patient's body during interferential therapy.

2. The Background Art

For many years, medical therapists have used interferential electrical current therapy in treating various physiological aliments. For example, therapists have found such interferential therapy to be helpful in the treatment of both pain and edema.

Interferential electrical current therapy is typically carried out using two pairs of electrodes which are adapted to be secured directly to a patient's body. During treatment of the patient, a separate electrical signal passes through the patient's body between each pair of electrodes. Importantly, the two electrical signals are selected such that a region of beneficial interference is provided in the patient's body to effect the desired treatment.

For example, a first electrical signal having a substantially constant frequency may be passed through a portion of a patient's body between the first pair of electrodes. A second electrical signal is simultaneously passed through substantially the same portion of the patient's body between the second pair of electrodes. Significantly, the frequency of the second electrical signal differs from that of the first electrical signal by a predetermined amount. As a result, a region of beneficial interference is formed in the patient's body due to the interaction of the two electrical signals.

The desired difference between the frequencies of the two electrical signals generally depends upon the nature of the physiological aliment being treated. When treating edema, for example, it is generally desirable that the difference between the frequencies of the two electrical signals be within the range from approximately 0 to 10 Hertz. When treating pain, on the other hand, it is typically desirable that the difference in frequencies be within in the range of from approximately 80 to 150 Hertz.

When using interferential electrical current therapy, a therapist generally attempts to position the region of beneficial interference in the patient's body so as to coincide as closely as possible to the localized area of the patient's body under treatment. For example, if a patient is to undergo treatment for pain located in the shoulder area, the therapist would generally attempt to position the region of beneficial interference so as to lie in the patient's shoulder area. Unfortunately, the accurate positioning of the region of beneficial interference has heretofore proved extremely difficult.

A therapist has conventionally positioned the region of beneficial interference in a patient's body by attempting to select and adjust the position of each pair of electrodes. However, this prior art method for positioning the region of interference is both imprecise and unpredictable, since the path of an electrical signal through a patient's body is highly dependent upon the shape, structure, and conductivity of the surrounding tissue. Consequently, one cannot generally determine the location of the region of interference in a patient's body simply by observing the position of the electrodes.

The inherent difficulty of properly positioning the region of interference in a patient's body using conventional methods renders the process both tedious and time-consuming. It may, for example, be necessary to remove and reposition the electrodes several times before the region of interference is in adequately close proximity to the area of the patient's body under treatment. Even then, due to the unpredictability of the process, therapists must frequently settle for somewhat less than desirable positioning of the region of interference when treating a patient.

BRIEF SUMMARY AND OBJECTS OF THE INVENTION

In view of the foregoing, it is a primary object of the present invention to provide a system and method for accurately positioning the region of beneficial interference in a portion of the patient's body during interferential electrical current therapy.

It is also an object of the present invention to provide a system and method for positioning the region of beneficial interference in a patient's body during interferential electrical current therapy which does not require the removal of the electrodes from the patient's body.

Consistent with the forgoing objects, the present invention is directed to a system and method for interferential electrical current therapy wherein the region of beneficial interference may be positioned in the body of a patient by selectively controlling the electrical signal which is provided to each of two pairs of electrodes secured to the patient's body. Two electrical signals are provided which have frequencies that differ by a predetermined amount. The system comprises means for selectively amplifying, phase shifting, and mixing the second electrical signal with the first electrical signal and applying the mixed signal to the first pair of electrodes. The system further comprises means for selectively amplifying, phase shifting, and mixing the first electrical signal with the second electrical signal and applying the mixed signal to the second pair of electrodes.

The two pairs of electrodes are secured on a patient's body in proximity to the area under treatment. Thereafter, the region of beneficial interference can be selectively positioned in the patient's body by appropriately controlling the amplifying, phase shifting, and mixing of the electrical signals which are applied to each pair of electrodes.

These and other objects and features of the present invention will become more fully apparent from the following description and appended claims, taken in conjunction with the accompanying drawings.

DETAILED DESCRIPTION OF THE PREFERRED EMBODIMENTS

It will be readily appreciated that the components of the present invention, as generally described and illustrated in the figures herein, could be arranged and designed in a wide variety of different configurations. Thus, the following more detailed description of the embodiments of the system and method of the present invention, as represented in FIGS. 1 through 3, is not intended to limit the scope of the invention, as claimed, but it is merely representative of the presently preferred embodiments of the invention.

The presently preferred embodiments of the invention will be best understood by reference to the drawings, wherein like parts are designated with like numerals throughout.

Figure 1:
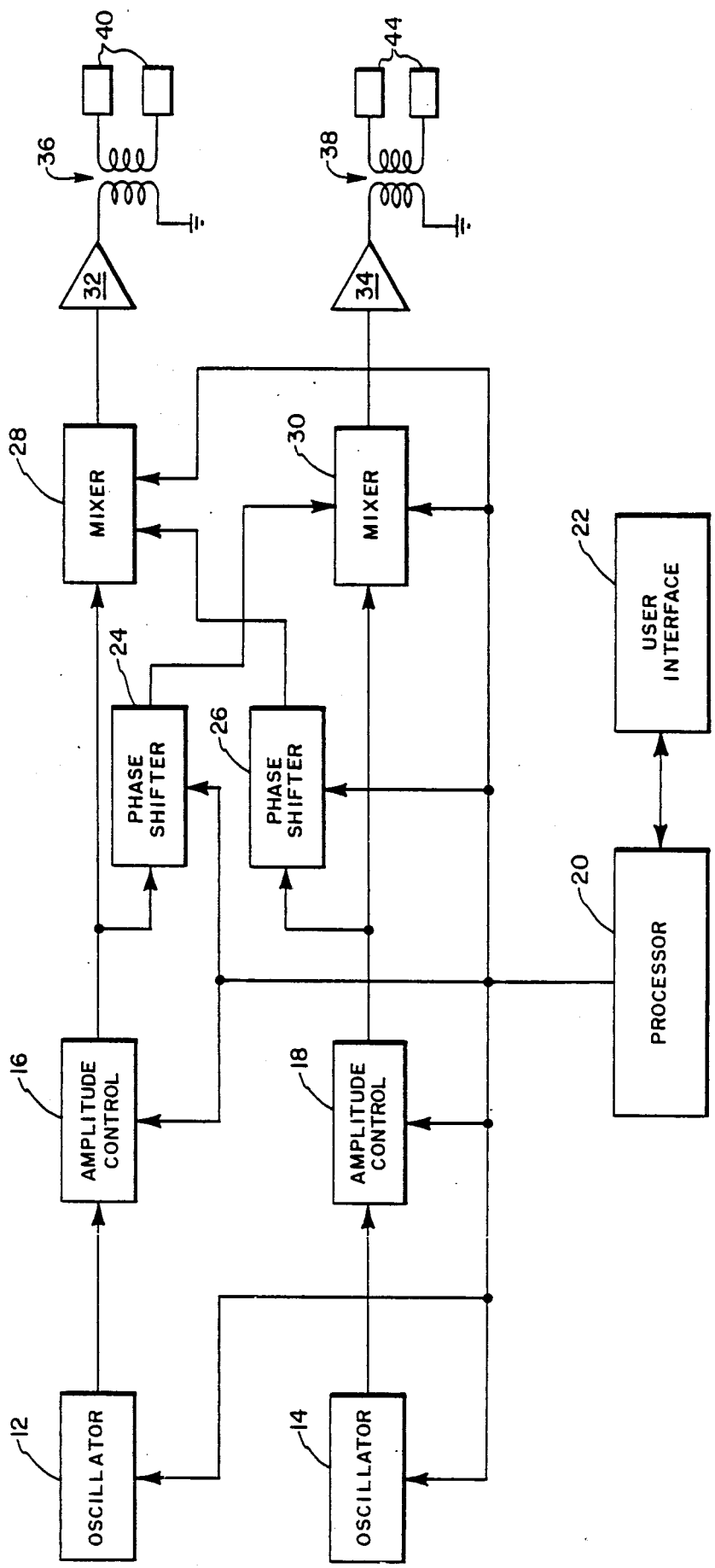
FIG. 1 is a general block diagram illustrating one presently preferred embodiment of the interferential electrical current therapy system of the present invention.
Figure 2C:
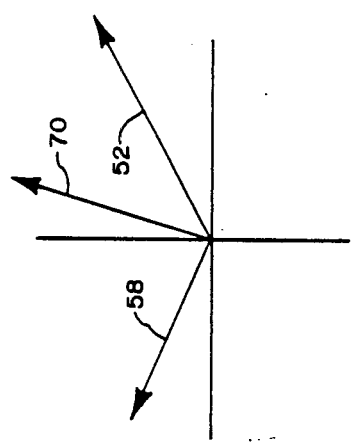
FIGS. 2A through 2C are vector diagrams illustrating the selective amplification, phase shifting, and mixing of electrical signals so as to effect an appropriate positioning of the region of beneficial interference in a patient's body when using the interferential electrical current therapy system of the present invention.
Figure 2B:
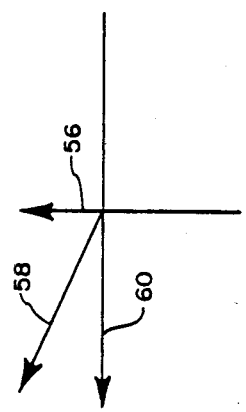

One presently preferred embodiment of the interferential electrical current therapy system of the present invention is illustrated in the block diagram of FIG. 1. As shown, the interferential electrical current therapy system comprises two oscillators 12 and 14. Oscillators 12 and 14 each generate an electrical signal having a selected frequency, the frequencies of the electrical signals generated by oscillators 12 and 14 differing by a desired amount.

For example, oscillator 12 might generate an electrical signal having a frequency of approximately 4.0 kilohertz ("kHz"). The frequency of the signal generated by oscillator 14 may then be selected so as to have the desired relationship relative to 4.0 kHz. For example, if a therapist is treating edema, the frequency of the signal generated by oscillator 14 should typically be within the range of from approximately 3990 Hertz ("Hz") to approximately 4010 Hz, whereby the difference between the frequencies generated by oscillators 12 and 14 is within the range of from approximately 0 to 10 Hz. When a therapist is treating pain, on the other hand, the frequency of the signal generated by oscillator 14 could be within the range of from approximately 4080 Hz to approximately 4150 Hz, whereby the difference between the freqencies generated by oscillators 12 and 14 is within the range of from approximately 80 to 150 Hz.

The signal generated by oscillator 12 is provided to an amplitude control device 16, and the signal from oscillator 14 is similarly provided to an amplitude control device 18. The output from amplitude control devices 16 and 18 are then provided to mixers 28 and 30, respectively.

Significantly, the output from amplitude control device 16 is provided through phrase shifter 24 to mixer 30, and the output of amplitude control device 18 is provided through phrase shifter 26 to mixer 28. Mixers 28 and 30 adjust the amplitude of their input signals and mix the signals together to provide a mixed signal output. In this way, the signal from oscillator 14 can be selectively amplified, phrase shifted, and mixed with the signal from oscillator 12 in mixer 28. Likewise, the signal from oscillator 12 can be selectively amplified, phase shifted, and mixed with the signal from oscillator 14 in mixer 30.

The output from mixers 28 and 30 are provided to output power amplifiers 32 and 34, respectively. The outputs from amplifiers 32 and 34 are then respectively provided to power transformers 36 and 38. The secondary coil of transformer 36 is connected to electrodes 40 to provide a first pair of electrodes for securement to a patient's body, and the secondary coil of transformer 38 is similarly connected to electrodes 44 to provide a second pair of electrodes.

The above-described components may be operated and controlled in a wide variety of different ways consistent with the present invention. In one presently preferred embodiment of the interferential therapy system of the present invention, these components are controlled using a processor 20 which is connected to a suitable user interface 22.

In using the interferential therapy system of the present invention, oscillators 12 and 14 are selectively controlled so as to generate electrical signals having the desired frequencies. The two electrical signals are then selectively amplified, phase shifted, and mixed such that the electrical signal which reaches the first pair of electrodes 40 and the second pair of electrodes 44 is a mixture of the electrical signals from both oscillators 12 and 14.

Electrodes 40 and 44 are secured to a patient in a conventional manner. Significantly, the region of beneficial interference may then be selectively positioned on the patient's body without removing the electrodes by selectively controlling the amplifying, phase shifting, and mixing of electrical signals generated by oscillators 12 and 14. This result may be appreciated by referring to the vector diagrams comprising FIGS. 2A through 2C.

Figure 2A:
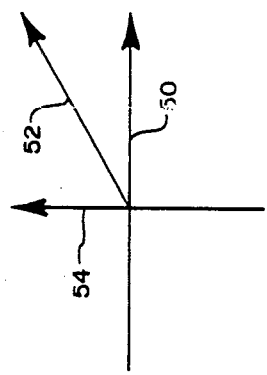
Figure 3A:
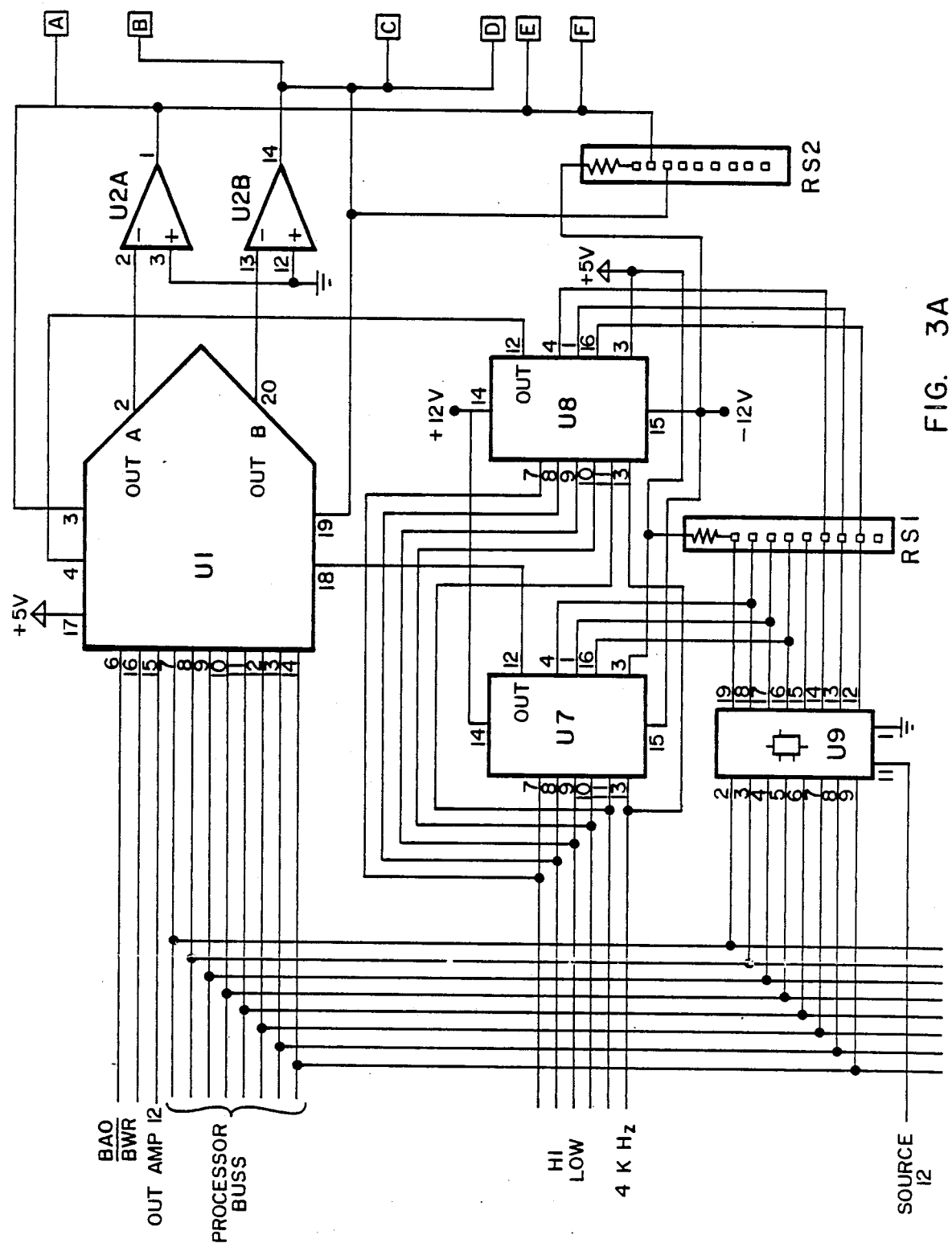
FIGS. 3A and 3B (hereinafter referred to collectively as FIG. 3), are an electrical schematic diagram illustrating one presently preferred configuration of an electrical circuit for use in connection with one presently preferred embodiment of the interferential electrical current therapy system of the present invention. (It should be noted that FIG. 3B is a continuation of the schematic diagram of FIG. 3A, tabs A through F of FIG. 3A corresponding to tabs A through F, respectively, of FIG. 3B, thereby illustrating the electrical interconnection between FIG. 3A and FIG. 3B).
Figure 3B:
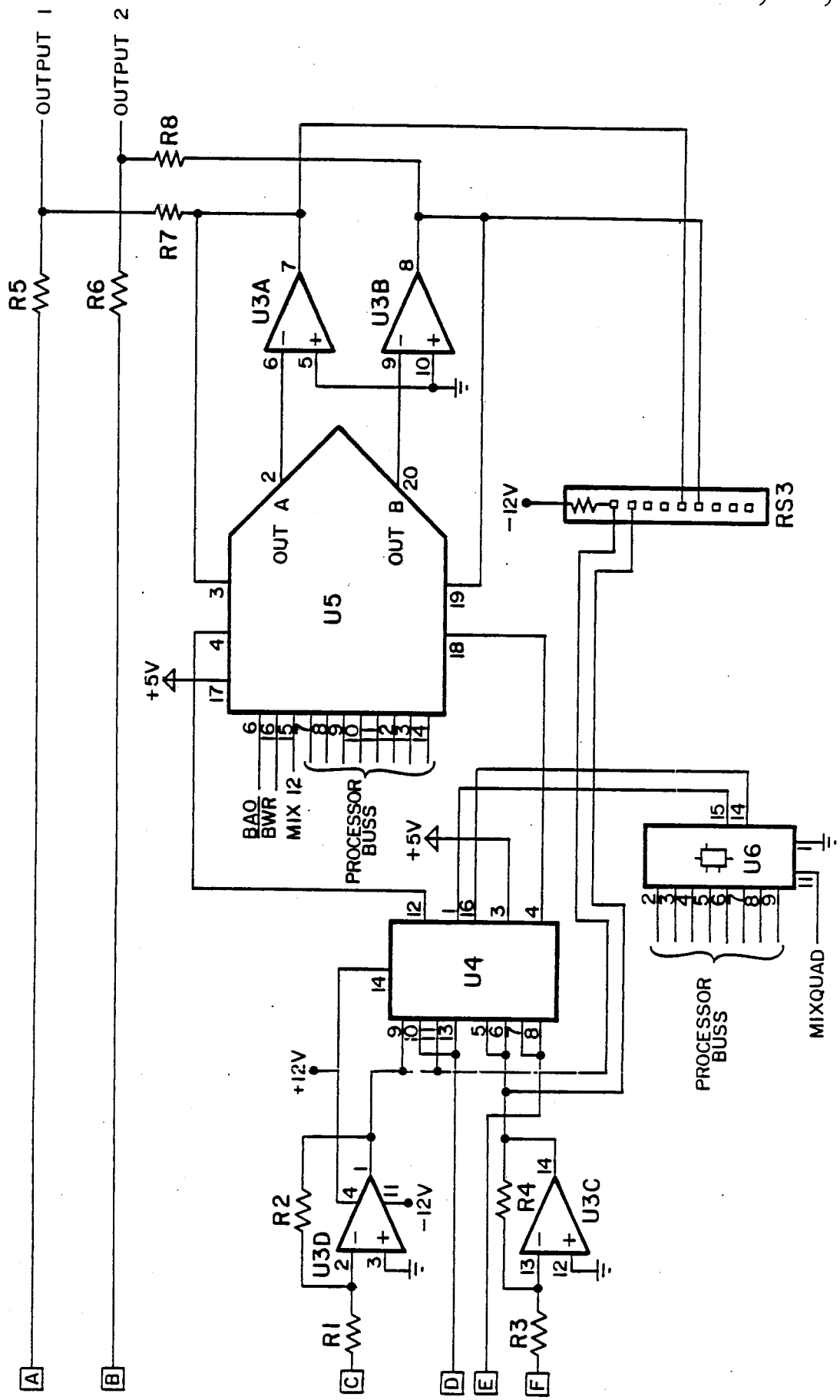

Vector 50 in FIG. 2A represents the signal generated by oscillator 12 in FIG. 1 as provided to mixer 28 through amplitude control 16. Vector 54 represents the electrical signal generated by oscillator 14 after passing through phase shifter 26 and mixer 28. Vector 52 represents the output from mixer 28 which is then provided through amplifier 32 and transformer 36 to electrodes 40.

Referring now to FIG. 2B, vector 56 represents the output of oscillator 14 which is provided through amplitude control 18 to mixer 30. Vector 60 represents the signal from oscillator 12 which is provided through amplitude control 16 and phase shifter 24 to mixer 30. The output from mixer 30 is represented by vector 58 which represents the signal provided through amplifier 34 and transformer 38 to electrodes 44.

During interferential therapy, the signal provided to electrodes 40 is combined in a patient's body with the signal provided to electrodes 44. The resultant signal is illustrated in FIG. 2C by vector 70 which is formed from combining vectors 52 and 58, discussed above.

Significantly, the position of the head of vector 70 is representative of the position of the region of beneficial interference which is created in a patient's body during therapy. Thus, as can be appreciated from FIGS. 2A through 2C, by appropriately amplifying, phase shifting, and mixing the signals generated by oscillators 12 and 14 so as to form vectors 52 and 58, the position of the region of beneficial interference, as represented by vector 70, can be selectively controlled.

When the present invention is configured as illustrated in FIG. 1, electrodes 40 and 44 may be secured to a patient, and the frequencies of the electrical signals produced by oscillators 12 and 14 may be selected so as to be within the desired range for the particular tretment. The therapist or the patient may then manipulate user interface 22 so as to accurately position the region of interference for maximum beneficial effect. Importantly, since the electrodes do not need to be removed from the patient, it is relatively fast and easy to determine when the region of interference has been properly positioned.

Any of a large number of components may be used to accomplish the functions described above in connection with FIG. 1. For example, processor 20 may comprise virtually any suitable processor, such as, for example, the processor currently availale through Hitachi as part number HB64180. Such a processor 20 can then control the components illustrated in FIG. 1 in a conventional manner.

Similarly, a large number of user interface devices can be used for user interface 22. For example, user interface 22 may comprise a conventional computer keyboard. User interface 22 might alternatively comprise a joy stick or an X-Y membrane potentiometer.

Oscillators 12 and 14 may comprise any suitable oscillators which generate electrical signals having the desired electrical frequencies. For example, oscillators 12 and 14 may comprise oscillators available from Exar as part number 2206.

As mentioned above, electrodes 40 and 44 are adapted to be secured directly to a patient's body. Suitable electrodes are readily available from various sources and may, for example, be formed of carbon. Alternatively, electrodes 40 and 44 may comprise conductive polymer pads.

Amplifiers 32 and 34 and transformers 36 and 38 are selected so as to supply electrodes 40 and 44 with the desired signal. For example, the signal at each pair of electrodes may be on the order of 150 to 200 volts peak-to-peak. In such case, amplifiers 32 and 34 may comprise SGS amplifiers which are currently available as part number TDA2040, and transformers 39 should preferably be capable of handling up to approximately seven watts power.

Amplitude control devices 16 and 18, phase shifters 24 and 26, and mixers 28 and 30 may be formed of a wide variety of different specific components. For example, those skilled in the art will readily appreciate that these components could be a combination of potentiometers and switches. Alternatively, such components may comprise other combinations of electronic circuitry which are adapted to appropriate control.

Reference is next made to FIG. 3 which illustrates in more detail one preferred embodiment of amplitude control devices 16 and 18, phase shifters 24 and 26, and mixers 28 and 30 which are illustrated in the block diagram of FIG. 1. Those of ordinary skill in the art will, of course, appreciate that various modifications to the detailed schematic diagram of FIG. 3 may be easily made without departing from the essential characteristics of the invention. Thus, the following description of the detailed schematic diagram of FIG. 3 is intended only as an example, and simply illustrates one presently preferred embodiment of a schematic diagram that is consistent with the forgoing description and the invention as claimed herein.

As illustrated in FIG. 3, the signals from suitable oscillators may be provided to multiplexers U7 and U8. These signals are then provided through digital-to-analog converter U1 and amplifiers U2A and U2B to outputs 1 and 2.

At the same time, the signals from U1 are provided through multiplexer U4 to a second digital-to-analog converter U5. Significantly, multiplexer U4, in combination with amplifiers U3C and U3D, effect either a 0° or 180° phase shift in the two signals being provided to U5. U5 then modifies the amplitude of the signals, and these signals are then mixed with the signals from U1 at outputs 1 and 2. Outputs 1 and 2 are connected through suitable power amplifiers 32 and 34 and transformers 36 and 38 to suitable electrodes, as illustrated in FIG. 1.

Table 1 below identifies the specific electrical components illustrated in FIG. 3. In addition, resistors R1 through R8 may, for example, be 1 kilo-ohm resistors, and components RS1 through RS3 may comprise single in-line package resistors which likewise have a resistance valve of approximately 1 kilo-ohm.

TABLE I

| Integrated Circuit Components of FIG. 3 | |
|---|---|
| No. | Type |
| U1 | MP7528 |
| U2 | LM324 |
| U3 | LM324 |
| U4 | MP7502 |
| U5 | MP7528 |
| U6 | ALS574 |
| U7 | MP7501 |
| U8 | MP7501 |
| U9 | ALS574 |

From the above discussion, it will be appreciated that the present invention provides an interferential electrical current therapy system wherein the region of beneficial interference may be selectively positioned without the need for removing the electrodes from a patient's body. Advantageously, the positioning of the region of beneficial interference may be accomplished by appropriately mixing electrical signals. As a result, a significant disadvantage inherent in prior art devices is overcome.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An interferential therapy system, comprising:
a first pair of electrodes adapted to being secured to a patient's body;
means for generating a first electrical signal, the first electrical signal having a first frequency;
a second pair of electrodes adapted to being secured to a patient's body;
means for generating a second electrical signal, the second electrical signal having a second frequency which differs from the first frequency;
means for selectively amplifying, phase shifting, and mixing the second electrical signal with the first electrical signal and applying the mixed electrical signal to the first pair of electrodes; and
means for selectively amplifying, phase shifting, and mixing the first electrical signal with the second electrical signal and applying the mixed electrical signal to the second pair of electrodes, whereby a region of therapeutic interference is selectively positioned on the body of the patient.

2. An interferential therapy system as defined in claim 1 wherein the first pair of electrodes comprise carbon electrodes.

3. An interferential therapy system as defined in claim 1 wherein the first pair of electrodes comprise conductive polymer pads.

4. An interferential therapy system as defined in claim 1 wherein the means for generating a first electrical signal and the means for generating a second electrical signal comprise a first variable frequency oscillator and a second variable frequency oscillator, respectively.

5. An interferential therapy system as defined in claim 1 wherein the means for selectively amplifying, phase shifting and mixing the second electrical signal with the first electrical signal comprises:
   an amplitude control circuit;
   a phase shifter circuit; and
   a mixer circuit.

6. An interferential therapy system as defined in claim 1 further comprising processor means for controlling the operation of the means for selectively amplifying, phase shifting, and mixing the second electrical signal with the first electrical signal and for controlling the operation of the means for selectively amplifying, phase shifting, and mixing the first electrical signal with the second electrical signal.

7. An interferential therapy system as defined in claim 6 wherein the processor means further comprises an X-Y positioning input device.

8. An interferential therapy system as defined in claim 1 further comprising a first power amplifier circuit connected between the first pair of electrodes and the means for selectively amplifying, phase shifting, and mixing the second electrical signal with the first electrical signal.

9. An interferential therapy system as defined in claim 8 wherein the first power amplifier circuit comprises a trnsformer conveying the output of the power amplifier circuit to the first pair of electrodes.

10. A method for selectively positioning a region of therapeutic interference on the body of a patient in connecting with the use of an interferential therapy system comprising:
   a first pair of electrodes adapted to being secured to a patient's body;
   means for generating a first electrical signal, the first electrical signal having a first frequency;
   a second pair of electrodes adapted to being secured to a patient's body; and
   means for generating a second electrical signal, the second electrical signal having a second frequency which differs from the first frequency;
   the method comprising the steps of:
   selectively amplifying, phase shifting, and mixing the second electrical signal with the first electrical signal and applying the mixed signal to the first pair of electrodes; and
   selectively amplifying, phase shifting, and mixing the first electrical signal with the second electrical signal and applying the mixed signal to the second pair of electrodes.

11. A method for selectively positioning a region of therapeutic interference on the body of the patient as defined in claim 10 further comprising the step of securing the first pair and the second pair of electrodes to the patient's body.

12. A method for selectively positioning a region of therapeutic interference on the body of the patient as defined in claim 10 wherein the step of selectively amplifying, phase shifting, and mixing the first electrical signal with the second electrical signal comprises the steps of:
   adjusting the relative amplitudes of the first electrical signal and the second electrical signal;
   modifying the relative phase of the first electrical signal and the second electrical signal; and
   mixing the amplitude adjusted and phase modified first and second electrical signals to produce a first mixed signal.

13. A system for providing interferential electrical current therapy to the human body, the system comprising:
   a first oscillator being adapted for generating a first electrical signal having a first frequency;
   a second oscillator being adapted for generating a second electrical signal having a second frequency which differs from the first frequency;
   first amplitude control means, connected to an output of the first oscillator, for adjusting the amplitude of the first electrical signal;
   second amplitude control means, connected to an output of the second oscillator, for adjusting the amplitude of the second electrical signal;
   first phase shifting means, connected to an output of the first amplitude control means, for shifting the phase of the first electrical signal;
   second phase shifting means, connected to an output of the second amplitude control means, for shifting the phase of the second electrical signal;
   first mixing means, receiving the outputs of the first amplitude control means and the second phase shifting means, for producing a first mixed output signal;
   second mixing means, receiving the outputs of the second amplitude control means and the first phase shifting means, for producing a second mixed output signal;
   a first pair and a second pair of electrodes adapted for attachment to the body;
   first outputting means for communicating the first mixed output signal to the first pair of electrodes;
   second outputting means for communicating the second mixed output signal to the second pair of electrodes; and
   control means for controlling the first and second oscillators, the first and second amplitude control means, the first and second phase shifting means, the first and second mixing means, and the first and second outputting means such that the location of the interferential therapy may be moved to any one of a plurality of locations within the body.

14. An interferential therapy system as defined in claim 13 wherein the first and second oscillators comprise a first variable frequency oscillator and a second variable frequency oscillator, respectively.

15. An interferential therapy system as defined in claim 13 wherein the control means comprises an X-Y positioning input device.

* * * * *